(12) United States Patent
Bernhardt et al.

(10) Patent No.: US 10,159,452 B2
(45) Date of Patent: Dec. 25, 2018

(54) CORRECTION OF AN X-RAY IMAGE FOR EFFECTS OF AN ANTI-SCATTER GRID

(71) Applicants: Philipp Bernhardt, Forchheim (DE); Dirk Ertel, Forchheim (DE)

(72) Inventors: Philipp Bernhardt, Forchheim (DE); Dirk Ertel, Forchheim (DE)

(73) Assignee: Siemens Healthcare GmbH, Erlangen (DE)

( * ) Notice: Subject to any disclaimer, the term of this patent is extended or adjusted under 35 U.S.C. 154(b) by 56 days.

(21) Appl. No.: 15/491,684

(22) Filed: Apr. 19, 2017

(65) Prior Publication Data

US 2017/0296131 A1    Oct. 19, 2017

(30) Foreign Application Priority Data

Apr. 19, 2016 (DE) .............................. 102016206559

(51) Int. Cl.
*G06K 9/00* (2006.01)
*A61B 6/00* (2006.01)
(Continued)

(52) U.S. Cl.
CPC .......... *A61B 6/4291* (2013.01); *A61B 6/4441* (2013.01); *A61B 6/488* (2013.01);
(Continued)

(58) Field of Classification Search
None
See application file for complete search history.

(56) References Cited

U.S. PATENT DOCUMENTS

| 5,050,198 A | 9/1991 | Honda |
| 6,285,781 B1 | 9/2001 | Yamazaki |

(Continued)

FOREIGN PATENT DOCUMENTS

| DE | 69014354 T2 | 7/1995 |
| DE | 69836931 T2 | 11/2007 |

(Continued)

OTHER PUBLICATIONS

European Search Report for European Application No. 17162858.9-1906, dated Jul. 4, 2017.
(Continued)

*Primary Examiner* — Sean M Conner
(74) *Attorney, Agent, or Firm* — Lempia Summerfield Katz LLC

(57) ABSTRACT

A method for correction of an x-ray image recorded with an x-ray device with an anti-scatter grid for effects of the anti-scatter grid is provided. The anti-scatter grid has a spatially periodically repeating geometrical embodiment, and a calibration image recorded without an imaging object is used. The calibration image and the x-ray image are transformed by a transformation into the position frequency space. In the position frequency space, adaptation parameters describing changes of the calibration image optimizing a measure of matching between the x-ray image and the calibration image are established. For correction, the adapted calibration image is subtracted from the x-ray image, and the x-ray image is transformed back into the position space again using an inverse of the transformation.

18 Claims, 3 Drawing Sheets

(51) Int. Cl.
*G06T 5/00* (2006.01)
*G06T 5/10* (2006.01)
*G06T 5/50* (2006.01)
*H04N 5/217* (2011.01)
*H04N 5/32* (2006.01)
*H04N 5/365* (2011.01)
*H04N 17/00* (2006.01)

(52) U.S. Cl.
CPC .......... *A61B 6/5252* (2013.01); *A61B 6/5258* (2013.01); *A61B 6/5282* (2013.01); *A61B 6/54* (2013.01); *A61B 6/585* (2013.01); *G06T 5/002* (2013.01); *G06T 5/10* (2013.01); *G06T 5/50* (2013.01); *H04N 5/217* (2013.01); *H04N 5/32* (2013.01); *G06T 2207/10116* (2013.01); *G06T 2207/20048* (2013.01); *G06T 2207/20056* (2013.01); *G06T 2207/20064* (2013.01); *G06T 2207/20212* (2013.01); *G06T 2207/20224* (2013.01); *G06T 2207/30004* (2013.01); *H04N 5/365* (2013.01); *H04N 17/002* (2013.01)

(56) References Cited

U.S. PATENT DOCUMENTS

| | | |
|---|---|---|
| 6,333,990 B1 | 12/2001 | Yazici et al. |
| 2003/0152259 A1 | 8/2003 | Belykh et al. |
| 2005/0031182 A1 | 2/2005 | Inoue |
| 2006/0233453 A1 | 10/2006 | Behiels et al. |
| 2010/0104165 A1* | 4/2010 | Takahashi ............ G06T 5/002 382/132 |
| 2012/0206630 A1* | 8/2012 | Nguyen ................ H04N 1/409 348/241 |
| 2013/0148786 A1 | 6/2013 | Kruschel et al. |
| 2014/0050300 A1* | 2/2014 | Hasegawa ............ G01N 23/04 378/62 |

FOREIGN PATENT DOCUMENTS

| | | |
|---|---|---|
| DE | 102011088265 A1 | 6/2013 |
| DE | 102013223392 A1 | 9/2014 |
| EP | 0962888 A2 | 12/1999 |
| EP | 1372108 A2 | 12/2003 |
| EP | 1505540 A2 | 2/2005 |
| JP | H11146277 A | 5/1999 |

OTHER PUBLICATIONS

German Office Action for German Application No. 10 2016 206 559.9, dated Nov. 22, 2016, with English Translation.

* cited by examiner

CORRECTION OF AN X-RAY IMAGE FOR EFFECTS OF AN ANTI-SCATTER GRID

This application claims the benefit of DE 10 2016 206 559.9, filed on Apr. 19, 2016, which is hereby incorporated by reference in its entirety.

BACKGROUND

The present embodiments relate to correction of an x-ray image recorded with an x-ray device with an anti-scatter grid for effects of the anti-scatter grid.

In x-ray imaging, anti-scatter grids are already widely known in the prior art for reducing disruptive amounts of scattered radiation in the x-ray image obtained. Anti-scatter grids may be used, for example, in the area of angiography and radiography imaging. Known technical realizations mostly employ anti-scatter grids that use lead lamellas that may be manufactured especially thin for x-ray absorption. Although the lamellas have a very small strip width, the structures of the anti-scatter grid formed by the lamellas are to be taken into account accordingly during the calibration of the imaging x-ray device.

The simple geometrical structure and the thin strip width in known anti-scatter grids already enables an adequate image quality of the ultimate x-ray images to be insured by a conventional calibration, in which a calibration image of just the anti-scatter grid (e.g., without an imaging object) is to be recorded. The calibration image may later be subtracted from the actual x-ray image to remove the contributions of the anti-scatter grid and to obtain a corrected x-ray image. Then, the lamella structures of the anti-scatter grid are no longer recognizable in clinical x-ray images.

The restricted geometrical structure provides that the proportion of scattered radiation in the x-ray images recorded using a conventional anti-scatter grid continues to be quite high. The image quality may be very much adversely affected, which is shown, for example, in strongly-absorbing imaging objects (e.g., extremely obese patients).

Therefore, current approaches have been proposed, in which far more complex geometrical structures are used within anti-scatter grids to improve the absorption behavior. Absorption materials are also employed in such cases, which may be realized with higher strip widths. The complex geometries and, if necessary, greater strip widths make a calibration or the use of calibration images much more difficult, however.

Added to this effect is the fact that, with many x-ray devices (e.g., C-arm x-ray devices), the recording arrangement including the x-ray emitter and the x-ray detector may be put into different positions to be able to record the imaging object (e.g., a patient) from different projection directions. In such cases, mechanical effects (e.g., from gravity acting elsewhere) may come into play if different recording geometries are used when compared to the calibration image. While this would have a small influence with anti-scatter grids with more simple structures and/or extremely thin lead lamellas, with more complex geometrical structures and/or larger strip widths, a greater restriction of the image quality may arise. These types of changes to the recording geometries may also be the result of ageing effects of the x-ray device.

SUMMARY AND DESCRIPTION

The scope of the present invention is defined solely by the appended claims and is not affected to any degree by the statements within this summary.

The present embodiments may obviate one or more of the drawbacks or limitations in the related art. For example, improved reduction of image artifacts in x-ray images stemming from an anti-scatter grid is provided.

In one embodiment, the calibration image and the x-ray image are be transformed by a transformation into the position frequency space. Adaptation parameters describing changes to the calibration image optimizing a measure of matching between the x-ray image and the calibration image are established in the position frequency space. The adapted calibration image is subtracted from the x-ray image for correction, and the x-ray image is transformed back into the position space again by applying the inverse of the transformation.

This method thus makes possible an adaptive image correction for reducing artifacts caused by the anti-scatter grid. The correction may be carried out in the frequency space. Through a corresponding transformation, specific characteristics of the anti-scatter grid are exploited, so that there may be an adequate correction of the medical image data of the x-ray image. This also makes it possible to use anti-scatter grids with a complex structure and innovative materials in the field of interventional radiology and also in other medical applications in which a high image quality is to be provided. The use of improved anti-scatter grids made possible by this significantly reduces the scattered radiation and thus improves the image quality, which basically creates the possibility for a lower dose load on the patient.

Specific characteristics of the anti-scatter grid (e.g., based on the fact that, although there may be a complex geometry, repeating geometrical structures/embodiments occur in the position space) are mapped during a transformation into the frequency space with low unsharpness. The structures identifying the anti-scatter grid in the frequency space may in this way be identified in a simple manner, and the calibration image may be adapted in relation to the image features caused by the anti-scatter grid so that the calibration image lies as optimally as possible above the x-ray image, covering the same area. By subtraction, the image artifacts (e.g., artifacts that arise through the anti-scatter grid) may thus be removed. The corresponding adaptations to the calibration image are described here by adaptation parameters that may also describe effects possibly occurring in the frequency space (e.g., a displacement or rotation of a component of the recording arrangement and the like).

The adaptation parameters may be adapted in such cases as free parameters in an iterative (e.g., optimization) method, so that there may be adequate correction of the current x-ray image in that the corresponding amounts may be subtracted in the frequency space itself. As already mentioned, the adaptation parameters involve such free parameters that describe the deviation of the different image acquisition states and thus the changed situation between the current recording geometry and the recording geometry during the calibration of the x-ray device (e.g., the recording of the calibration image). After the subtraction of the adapted calibration image from the current x-ray image in the frequency space, the corrected x-ray image is transformed back into the position space using inverse transformation and may then continue to be processed accordingly.

The method may also work with a number of calibration images. The method described here may be applied without any restriction to general applicability in all imaging x-ray devices (e.g., in x-ray devices with a C-arm, CT devices, radiography systems and the like).

Since the correction is established in the frequency space, problematic interpretations in the position space are avoided, and the binding to the pixel matrix of the x-ray image previously present is canceled. In addition, as will be shown in greater detail, many free parameters in the frequency space correspond to changes of the recording geometry arising correspondingly and/or other recording parameters.

The phase of the calibration image in the position frequency space and/or the intensity of the calibration image in the position frequency space and/or a rotation of the calibration image in the position frequency space may be able usable as adaptation parameters. It is precisely when used in an x-ray device with a C-arm that the anti-scatter grid, as well as other parts of the recording arrangement, is subjected to strong mechanical influences (e.g., by the different angulations of the C-arm). This may easily cause mechanical displacements of the anti-scatter grid, for example, that are represented in the frequency space by a phase shift. This provides that the artifact contributions exhibit a phase displacement compared to the actual calibration image. If the phase in the calibration image in the position frequency space is thus considered as an adaptation parameter, these types of effects may easily be taken into consideration by corresponding adaptation of the calibration image. Also, the intensity of the calibration images may have to be adapted if, for example, the different absorption behavior of patient or general imaging objects leads to very different signal strengths at the x-ray detector (e.g., including anti-scatter grid). Because of these different signal strengths, the artifact contributions are then also represented with different intensity, so that a measure for the intensity may be included in the calibration image in the frequency space as an adaptation parameter. A rotation of the calibration image in the position frequency space may also be described by the adaptation parameters, since a rotation in the position space is also able to be represented as a rotation in the position frequency space. Further adaptation parameters may also be provided.

Basically known optimization methods may be used as the optimization method for determining the optimum values for the adaptation parameters and thus of the optimally adapted calibration image (e.g., gradient-based optimization methods and/or Newtonian optimization methods).

A usual, two-dimensional Fourier transformation may be used as the transformation. Within the framework of the present embodiments, a geometry transformation taking into account at least one geometry characteristic of the anti-scatter grid (e.g., a wavelet transformation) may be used as the transformation. In this case, a dedicated wavelet that has an appropriate correspondence with the periodically spatially repeating geometrical embodiment (e.g., with a geometrical structure repeating in a grid pattern) may be used. This makes it possible to minimize the unsharpnesses with which the calibration image is mapped in the frequency space, so that it may be provided that the image correction is restricted to the characteristic frequencies induced by the anti-scatter grid and by a periodically spatially repeating geometrical embodiment. A function describing the periodically repeating geometrical basic pattern of the anti-scatter grid may be used as a wavelet of a wavelet transformation. Within the framework of the wavelet transformation or generally of the geometry transformation, a correlation calculation with a signal (e.g., the wavelet) that corresponds to the geometrical structure (e.g., a honeycomb in a honeycomb pattern of the anti-scatter grid) may be carried out. Through this correlation, which may be carried out, as is basically known, in a number of scaling steps, a type of optimization is already provided. The establishment of the adaptation parameter may thus be done at least partly within the framework of carrying out the wavelet transformation.

A further advantage of using a geometry transformation, or, specifically, a wavelet transformation, is that this may already be locally embodied. However, within the framework of the present embodiments, the transformation may be applied locally (e.g., as a windowed transformation). In this way, for example, noise effects (e.g., in the edge areas of the x-ray image) may be handled better, so that a local optimization may be provided. For example, a windowed two-dimensional Fourier transformation may thus be employed.

A window function used for local application may have an extent of a geometrical basic pattern of the anti-scatter grid or a multiple of this value and/or is selected as the form of the basic pattern or a surrounding cell circumscribing this. In this case, the basic pattern corresponds, as already mentioned, to the structure or embodiment repeating itself spatially periodically (e.g., a honeycomb when a grid structure formed from honeycombs is used). Thus, a corresponding window transformation has an adequate correspondence with a grid pattern, so that, for example, the form of the window function may be the same as the periodically spatially repeated grid pattern; in this case, the actual size of the window function (e.g., its extent) may have a corresponding enlargement factor applied to the window function.

In one embodiment, results of a previous correction made to a preceding image may be used as start values for the adaptation parameters to be optimized. The method may thus be expanded by a type of memory element, which makes it possible adequately to initialize the adaptive method (e.g., the determination of the adaptation parameters maximizing the measure of matching). In this case, different embodiments may be provided.

Thus, an x-ray image recorded immediately before the current x-ray image may be used as a preliminary image. Thus, the result values of the adaptation parameters of a directly preceding recording (e.g., in fluoroscopy and/or repeated recordings) determined as optimizing are used as start values for the adaptation of the calibration image to the current (e.g., live) x-ray image, so that it is thus assumed that only a small change is to be obtained.

Within the framework of the present embodiments (e.g., in a calibration process), for different recording parameters of the x-ray device (e.g., describing the recording geometry), preliminary images may be recorded, and optimized adaptation parameters may be determined and stored as a database assigned to the recording parameters. The start values for the current x-ray image are selected from the database in accordance with the current recording parameters. Thus, in this embodiment, a further calibration process is provided to fill a memory element with a database, in which at least partly the recording parameters describing the recording geometry are assigned start values for adapting the calibration image to the current x-ray image in the position frequency space. If the recording parameters are identically present in the database, the start values may be used directly; the start values assigned to the recording parameters of the database determined as closest to the current recording parameters may, however, always be used, and/or an interpolation or an extrapolation may be carried out, respectively.

The database thus forms a sort of look-up table. In this way, characteristic dependencies on the recording parameters may be taken into account especially advantageously and transferred to the adaptation as a starting point. In this case, there may also be a consideration of recording parameters extending beyond the recording geometry (e.g., a dependence of the intensity on the current absorption behavior of the x-rayed imaging object may be considered). In this way, a reliable, robust, and faster establishment of the optimizing values of the adaptation parameters may be provided.

In addition to the method, the present embodiments also relate to an x-ray device, having a control device embodied for carrying out the method. Thus, the correction of effects of an anti-scatter grid of the x-ray device, which may be provided on the detector side as part of a recording arrangement with an x-ray emitter and an x-ray detector, may be undertaken immediately at the x-ray device. The x-ray device may, for example, involve an x-ray device with a C-arm, on which an x-ray emitter and an x-ray detector are arranged opposite one another. The anti-scatter grid may, for example, be connected upstream of the x-ray detector placed on the detector or attached to the detector. All disclosure related to the method may be transferred analogously to the x-ray device, with which the advantages already stated may thus likewise be obtained.

A computer program is able to be loaded, for example, directly into a memory of a control device of an x-ray device and has a program for carrying out the acts of a method described herein when the computer program is executed in the control device of the x-ray device. If the computer program is provided with the calibration image and the x-ray image, the computer program may also be executed on another computing device (e.g., on an evaluation workstation). The computer program may be stored on an electronically-readable data medium (e.g., a non-transitory computer-readable storage medium) that includes electronically-readable control information stored thereon. The electronically-readable control information includes at least the computer program and is embodied such that, when the data medium is used in a control device of an x-ray device or another computing device, the control device or the other computer device carries out a method described herein. The disclosure related to the method also applies in relation to the computer program and the data medium.

DETAILED DESCRIPTION

Figure 1:
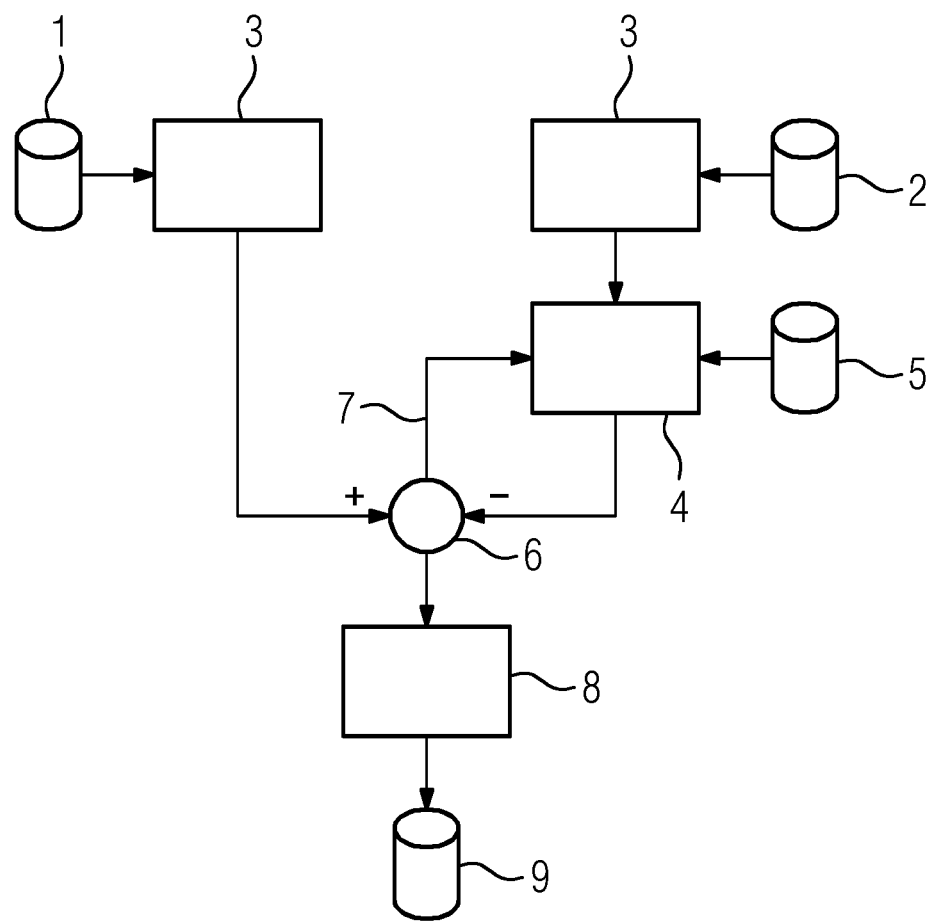
FIG. 1 shows a flowchart of a first exemplary embodiment of the method.

FIG. 1 shows a flowchart of a first exemplary embodiment of a method. The starting point is an x-ray image 1 that has been recorded with an x-ray device using an anti-scatter grid and is to be corrected with the aid of a calibration image 2 that only shows effects of the anti-scatter grid (e.g., has been recorded without an imaging object). Since changes may occur in the recording situation between the recordings of the calibration image 2, which may be stored in a memory device of the x-ray device, and the x-ray image 1, the calibration image 2 is to first be adapted before the calibration image 2 may be used for correction by being subtracted from the x-ray image 1. Both the x-ray image 1 and the calibration image 2 will initially be transformed in acts 3 into the position frequency space, where a windowed two-dimensional Fourier transformation is, for example, used as the transformation. The anti-scatter grid has a basic pattern repeating periodically as a type of grid (e.g., a honeycomb). The window function is oriented in an extent and signal form to this honeycomb, to make a local optimization possible.

If the x-ray image 1 and the calibration image 2 have first been transformed into the position frequency space, the calibration image 2 is adapted in accordance with act 4. This provides that adaptation parameters optimizing a measure of matching between the x-ray image 1 and the calibration image 2, which describe the adaption of the calibration image 2, is established in an optimization method.

To do this, start values are first selected from a database 5. The database 5 contains suitable start values, which are assigned to sets of recording parameters. The start values assigned to the set of recording parameters best corresponding to the current recording parameters are selected and applied at the beginning of the adaptation in act 4. As indicated by the circle 6, the calibration image 2 adapted by the start values are taken away from the x-ray image 1, and this is done in the position frequency space. The maximization of the measure of matching thus corresponds, for example, to a minimization of the difference. The optimization, which may be done in accordance with a usual optimization method, is symbolized by the arrow 7.

Adaptation parameters are, for example, considered to be the phase of the calibration image 2, the intensity of the calibration image 2, and a rotation of the calibration image 2 in the frequency space in each case. A phase displacement corresponds to a displacement in the position space, intensity changes may be produced by the imaging object to be irradiated (e.g., a patient), and a rotation in the frequency space maps a rotation in the position space.

If a sufficient maximization of the measure of matching is established by an abort criterion of the optimization method, the adaption of the calibration image 2 is concluded, and the corresponding difference forms the corrected x-ray image in the position frequency space. Thus, the inverse of the windowed two-dimensional Fourier transformation of act 3 is applied in act 8 to obtain the corrected x-ray image 9 in the position space.

Figure 2:
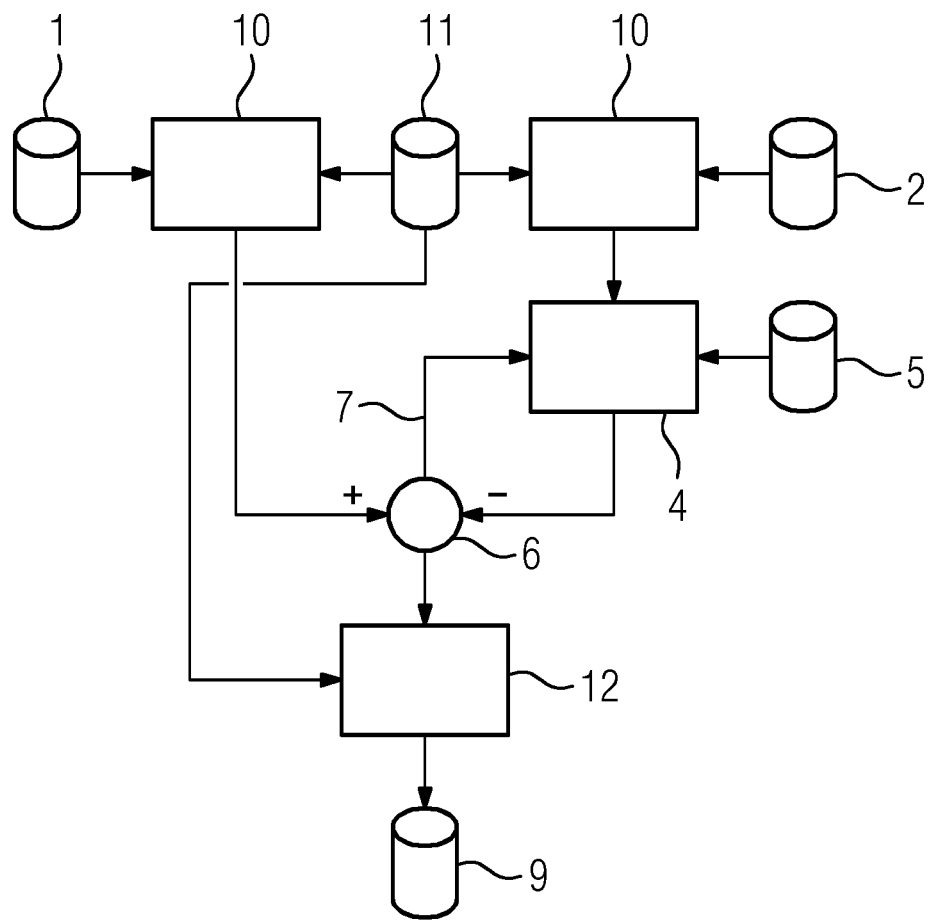
FIG. 2 shows a flowchart of a second exemplary embodiment of the method.

FIG. 2 shows a further embodiment of the method, which differs from the embodiment of FIG. 1 in the type of transformation into the position frequency space. In act 10, a wavelet transformation is applied. The wavelet 11 used has been selected using background knowledge about the anti-scatter grid. For example, the signal form of the wavelet may correspond to the already mentioned, spatially periodically repeating basic pattern in the anti-scatter grid. In this way, the frequency structures induced by the anti-scatter grid 11 may be obtained clearly in the position frequency space, thus essentially focusing on the image effects (e.g., artifacts) induced by the anti-scatter grid and thus achieving an improved optimization. The improved optimization may in part already take place within the framework of the transformation itself. For the sake of clarity, this is not shown in any greater detail. Accordingly, in act 12, the inverse wavelet transformation is also applied to obtain the corrected x-ray image 9.

Figure 3:
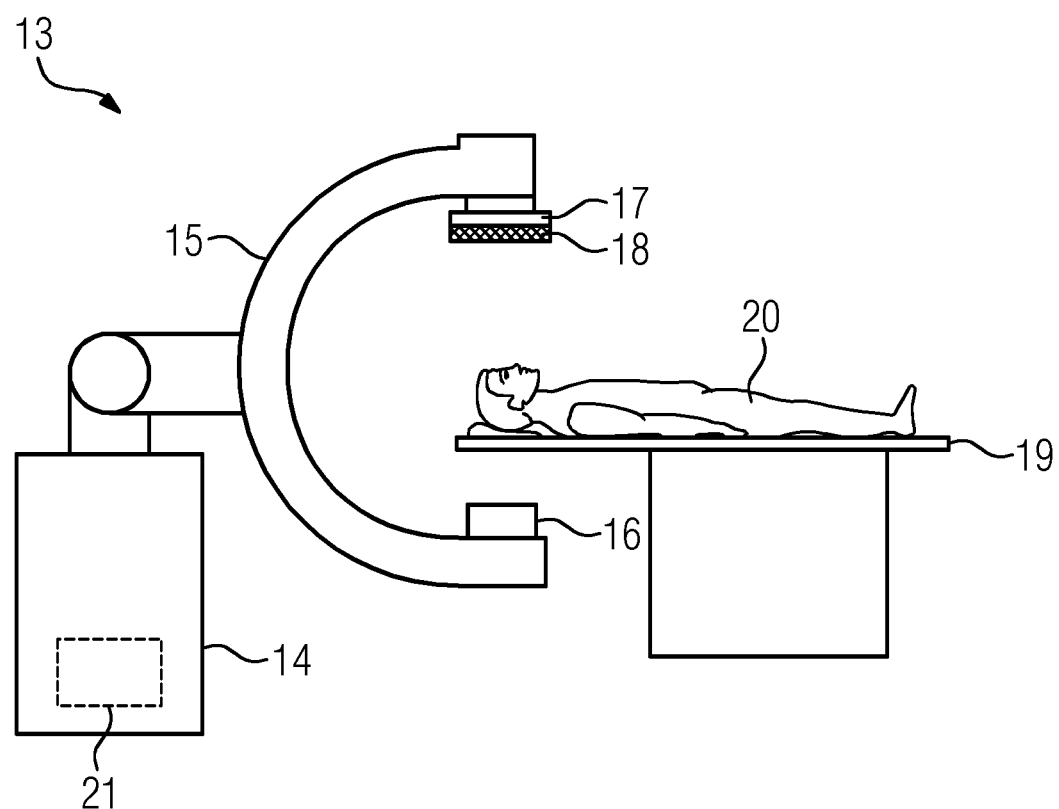
FIG. 3 shows one embodiment of an x-ray device.

FIG. 3 shows a basic sketch of one embodiment of an x-ray device 13. The x-ray device 13 includes a C-arm 15 arranged on a plinth 14, on which an x-ray emitter 16 and an x-ray detector 17 are arranged opposite one another. Arranged mounted on the x-ray detector 17 in FIG. 3 is an anti-scatter grid 18 that has a spatially periodically repeating structure (e.g., a geometric basic pattern) as a type of grid.

Using the C-arm 15, the recording arrangement formed by the x-ray emitter 16 and the x-ray detector 17 may be moved into recording positions defining different recording geometries in relation to a patient 20 supported on a patient couch 19.

The operation of the x-ray device 13 is controlled via a control device 21 that is embodied for carrying out the method. That provides that whenever a new x-ray image has been recorded, a calibration image stored in a memory device of the control device 21 is configured in the frequency space so that there will be a best-possible correction of the image effects (e.g., artifacts) caused by the anti-scatter grid 18.

A method described herein may also be present in the form of a computer program that implements the method on the control device 21 when the program is executed on the control device 21. Likewise, an electronically-readable data medium (not shown) with electronically-readable control information stored thereon may be available, which at least includes a described computer program and is embodied such that, when the data medium is used in the control device 21 of the x-ray device 13, the computer program carries out a described method.

Although the invention has been illustrated and described in greater detail by the exemplary embodiments, the invention is not restricted by the disclosed examples. Other variations may be derived herefrom by the person skilled in the art without departing from the scope of protection of the invention.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for correction of an x-ray image of an imaging object recorded with an x-ray device, the x-ray device including an anti-scatter grid, wherein the anti-scatter grid includes a spatially periodically repeating geometrical configuration, the method comprising:
   transforming a calibration image and the x-ray image by a transformation from a position space to a position frequency space, the calibration image being recorded without the imaging object;
   establishing, in the position frequency space, adaptation parameters describing changes to the calibration image optimizing a measure of matching between the x-ray image and the calibration image; and
   correcting the x-ray image, the correcting of the x-ray image comprising subtracting, in the position frequency space, the adapted calibration image from the x-ray image and transforming the corrected x-ray image back into the position space using an inverse of the transformation.

2. The method of claim 1, wherein a phase of the calibration image in the position frequency space, an intensity of the calibration image in the position frequency space, a rotation of the calibration image in the position frequency space, or any combination thereof is used as adaptation parameters.

3. The method of claim 1, wherein a two-dimensional Fourier transformation or a geometry transformation is used as the transformation.

4. The method of claim 3, wherein the geometry transformation is used as the transformation, and
   wherein the geometry transformation includes a wavelet transformation taking account of at least one geometry characteristic of the anti-scatter grid.

5. The method of claim 4, wherein a function describing a periodically repeating geometric pattern of the anti-scatter grid is used as a wavelet of the wavelet transformation, the adaptation parameters are established at least partly within a framework of carrying out the wavelet transformation, or a combination thereof.

6. The method of claim 1, wherein the transformation is applied locally.

7. The method of claim 6, wherein the transformation is applied locally as a windowed transformation.

8. The method of claim 7, wherein a window function used for the local application features an extension of a geometrical basic pattern of the anti-scatter grid or a multiple of a value of the extension, is selected as mapping a shape of the geometrical basic pattern or of a cell circumscribing the geometrical basic pattern, or a combination thereof.

9. The method of claim 1, wherein results of a previous correction to a preliminary image is used as start values for the adaptation parameters to be optimized.

10. The method of claim 9, wherein an x-ray image recorded immediately before the current x-ray image is used as a preliminary image.

11. The method of claim 9, wherein in a calibration process for different recording parameters of the x-ray device describing a recording geometry, preliminary images are recorded and optimized adaptation parameters are determined and stored assigned to the recording parameters as a database,
   wherein the start values for the current x-ray image are selected from the database in accordance with the current recording parameters.

12. An x-ray device comprising:
   an anti-scatter grid including a spatially periodically repeating geometrical configuration; and
   a controller configured to correct an x-ray image of an imaging object recorded with the x-ray device, the correction comprising:
   transformation of a calibration image and the x-ray image by a transformation from a position space to a position frequency space, the calibration image being recorded without the imaging object;
   establishment, in the position frequency space, of adaptation parameters describing changes to the calibration image optimizing a measure of matching between the x-ray image and the calibration image; and
   correction of the x-ray image, the correction of the x-ray image comprising subtraction in the frequency space, of the adapted calibration image from the x-ray image and transformation of the corrected x-ray image back into the position space using an inverse of the transformation.

13. A computer program product comprising a non-transitory computer-readable storage medium, the computer-readable storage medium storing instructions executable by a computing device to correct an x-ray image of an imaging object recorded with an x-ray device, the x-ray device including an anti-scatter grid, wherein the anti-scatter grid includes a spatially periodically repeating geometrical configuration, the instructions comprising:

transforming a calibration image and the x-ray image by a transformation from a position space to a position frequency space, the calibration image being recorded without the imaging object;

establishing, in the position frequency space, adaptation parameters describing changes to the calibration image optimizing a measure of matching between the x-ray image and the calibration image; and correcting the x-ray image, the correcting of the x-ray image comprising subtracting, in the position frequency space, the adapted calibration image from the x-ray image and transforming the corrected x-ray image back into the position space using an inverse of the transformation.

14. A non-transitory computer-readable storage medium storing instructions executable by a computing device to correct an x-ray image of an imaging object recorded with an x-ray device, the x-ray device including an anti-scatter grid, wherein the anti-scatter grid includes a spatially periodically repeating geometrical configuration, the instructions comprising:

transforming a calibration image and the x-ray image by a transformation from a position space to a position frequency space, the calibration image being recorded without the imaging object;

establishing, in the position frequency space, adaptation parameters describing changes to the calibration image optimizing a measure of matching between the x-ray image and the calibration image; and correcting the x-ray image, the correcting of the x-ray image comprising subtracting, in the position frequency space, the adapted calibration image from the x-ray image and transforming the corrected x-ray image back into the position space using an inverse of the transformation.

15. The non-transitory computer-readable storage medium of claim 14, wherein a phase of the calibration image in the position frequency space, an intensity of the calibration image in the position frequency space, a rotation of the calibration image in the position frequency space, or any combination thereof is used as adaptation parameters.

16. The non-transitory computer-readable storage medium of claim 14, wherein a two-dimensional Fourier transformation or a geometry transformation is used as the transformation.

17. The non-transitory computer-readable storage medium of claim 16, wherein the geometry transformation is used as the transformation, and
wherein the geometry transformation includes a wavelet transformation taking account of at least one geometry characteristic of the anti-scatter grid.

18. The non-transitory computer-readable storage medium of claim 17, wherein a function describing a periodically repeating geometric pattern of the anti-scatter grid is used as a wavelet of the wavelet transformation, the adaptation parameters are established at least partly within a framework of carrying out the wavelet transformation, or a combination thereof.

* * * * *